US010261081B2

(12) United States Patent
Rowlen

(10) Patent No.: US 10,261,081 B2
(45) Date of Patent: Apr. 16, 2019

(54) LOW DENSITY MICROARRAYS FOR VACCINE RELATED PROTEIN QUANTIFICATION, POTENCY DETERMINATION AND EFFICACY EVALUATION

(75) Inventor: Kathy L. Rowlen, Boulder, CO (US)

(73) Assignee: INDEVR, INC., Boulder, CO (US)

( * ) Notice: Subject to any disclaimer, the term of this patent is extended or adjusted under 35 U.S.C. 154(b) by 551 days.

(21) Appl. No.: 13/494,802

(22) Filed: Jun. 12, 2012

(65) Prior Publication Data

US 2012/0316079 A1 Dec. 13, 2012

Related U.S. Application Data

(60) Provisional application No. 61/496,223, filed on Jun. 13, 2011.

(51) Int. Cl.
*G01N 33/68* (2006.01)
*G01N 33/569* (2006.01)

(52) U.S. Cl.
CPC ... *G01N 33/56983* (2013.01); *G01N 33/6845* (2013.01); *G01N 2333/11* (2013.01)

(58) Field of Classification Search
CPC ......... G01N 33/56983; G01N 33/6854; G01N 33/6845; G01N 2333/11
See application file for complete search history.

(56) References Cited

U.S. PATENT DOCUMENTS

| | | | |
|---|---|---|---|
| 2009/0124512 | A1 | 5/2009 | Rowlen et al. |
| 2009/0163375 | A1 | 6/2009 | Bowman et al. |

FOREIGN PATENT DOCUMENTS

| | | |
|---|---|---|
| KR | 10-2010-0074743 A | 7/2010 |
| KR | 2010/0074743 | 7/2010 |
| WO | 2000-04389 A2 | 1/2000 |
| WO | 2002-25287 A2 | 3/2002 |
| WO | 2005-007677 A2 | 1/2005 |
| WO | WO 2006/020126 | 2/2006 |
| WO | WO 2009/148395 | 12/2009 |
| WO | WO 2011/050463 | 5/2011 |

OTHER PUBLICATIONS

Wang et al., "Glycans on influenza hemagglutinin affect receptor binding and immune response", PNAS, vol. 106, No. 43, p. 18137-18142 (2009).*
Liang et al. "Glycan arrays: biological and medical applications", Current Opinion in Chemical Biology, vol. 12, p. 86-92 (2008).*
Kingsmore, "Multiplexed protein measurement: technologies and applications of protein and antibody arrays", Nature Reviews Drug Discovery, p. 1-11, (published online Mar. 17, 2006).*
Liang et al., "Quantitative analysis of carbohydrate-protein interactions using glycan microarrays: determination of surface and solution dissociation constants", Journal of the American Chemical Society, vol. 129, p. 11177-11184 (2007).*
Vester et al., "Quantitative analysis of cellular proteome alterations in human influenza A virus-infected mammalian cell lines", Proteomics, vol. 9, p. 3316-3327 (2009).*
Wang et al., "Array-Based Multiplexed Screening and Quantitation of Human Cytokines and Chemokines", Journal of Proteome Research, vol. 1, p. 337-343 (2002).*
Ueda et al., "Application of Subtype-Specific Monoclonal Antibodies for Rapid Detection and Identification of Influenza A and B Viruses", Journal of Clinical Microbiology, vol. 36, p. 340-344 (1998).*
Robinson et al., "Autoantigen microarrays for multiplex characterization of autoantibody responses", Nature, vol. 8, No. 3, p. 295-301 (2002).*
Wang et al., "Glycans on influenza hemaglutinin affect receptor binding and immune response", PNAS, vol. 106, p. 18137-18142 (2009).*
Liu et al., "Validation of a Fully Integrated Microfludic Array Device for Influenza A Subtype Identification and Sequencing", Analytical Chemistry, vol. 78, No. 12, (2006).*
Lv et al ; 2007; Expert Rev. Proteomics 4(4), 505-513.*
Korean Intellectual Property Office; International Search Report and Written Opinion of the International Searching Authority; dated Jan. 29, 2013; PCT/US2012/042093; 11 pp.
Supplementary European Search Report corresponding to European Patent Application No. EP12801262, dated Dec. 4, 2014.
M.B. Townsend et al., "Experimental Evaluation of the FluChip Diagnostic Microarray for Influenza Virus Surveillance," Aug. 2006, Journal of Clinical Microbiology, vol. 44, No. 8, pp. 2863-2871.
Australian Patent Examination Report No. 1 corresponding to Australian Patent Application AU 2012/271858, dated May 5, 2016.
P.H. Liang et al., "Quantitative Analysis of Carbohydrate-Protein Interactions Using Glycan Microarrays: Determination of Surface and Solution Dissociation Constants," Apr. 30, 2007, Journal of the American Chemical Society, vol. 127, pp. 11177-11184.

(Continued)

*Primary Examiner* — Julie Wu
*Assistant Examiner* — Carmencita M Belei
(74) *Attorney, Agent, or Firm* — Leydig, Voit & Mayer, Ltd.

(57) ABSTRACT

Methods for the quantification of influenza HA proteins and anti-influenza antibodies for the fields of vaccine-related protein quantification, potency determination, and efficacy evaluation are provided. According to the technology, quantification is achieved by providing capture agents attached to an array in a series of decreasing concentrations. Serial dilutions of a reference material also may be introduced. The reference material within each solution binds to the capture agents on the array and is labeled with a label agent capable of producing a detectable signal used to construct a calibration curve. A target material of unknown concentration is introduced to a separate identical array, and the target material binds to the capture agents and also is labeled by a label agent to produce a detectable signal. The calibration curve based on the reference material is then utilized to determine the concentration of the target material without the need to perform replicate experiments.

31 Claims, 8 Drawing Sheets

(56) References Cited

OTHER PUBLICATIONS

Krammer et al. (Oct. 2013) "Influenza Virus Hemagglutinin Stalk-based Antibodies and Vaccines," Current Opinion in Virology 3(5):521-530.
Ekiert et al. (Apr. 10, 2009) "Antibody Recognition of a Highly Conserved Influenza Virus Epitope," Science 324(5924):246-251.
Nabel et al. (Dec. 2010) "Induction of Unnatural Immunity; Prospects for a Broadly Protective Universal Influenza Vaccine," Nature Medicine 16(12):1389-1391.

* cited by examiner (A)

(B)

Fluorescent label
Antibody label agent
Antibody target material
HA antigen capture agent

LOW DENSITY MICROARRAYS FOR VACCINE RELATED PROTEIN QUANTIFICATION, POTENCY DETERMINATION AND EFFICACY EVALUATION

STATEMENT REGARDING PRIORITY AND RELATED APPLICATIONS

The present application claims priority under 35 U.S.C. § 119 to U.S. Provisional Patent Application Ser. No. 61/496,223, filed Jun. 13, 2011, which is incorporated herein by reference as if set out in full.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. R43 AI102318 awarded by National Institutes of Health.

ABSTRACT

The invention provides array-based methods for the quantification of vaccine-related proteins for potency determination and efficacy evaluation. In certain embodiments, influenza HA proteins and anti-influenza antibodies can be quantified by providing a plurality of appropriate capture agents immobilized onto an array at a series of concentrations so as to generate a complete binding curve for a reference material that can then be utilized to determine the unknown concentration of a target species. In some embodiments, the capture agents are strain-specific influenza anti-HA antibodies. In other embodiments, the capture agents are universal anti-influenza antibodies. In other embodiments, the capture agents are sialic acid glycoproteins. In even other embodiments, the capture agents are influenza hemagglutinin proteins.

BACKGROUND

The FDA approved gold standard potency assay for influenza hemagglutinin protein-based vaccines is single radial immunodiffusion (SRID). SRID is a time and labor intensive assay, often requiring 2-3 days to complete and a minimum of 6 hours hands on time by well-trained analysts. In the SRID assay, viral antigen is applied to an agarose gel matrix that contains specific antibodies to the antigen being measured. The applied antigen diffuses radially, and interaction between antigen and antibody produces a zone of precipitation. The size of this precipitation zone is directly proportional to the amount of antigen applied. The assay is also separately performed a number of times on dilutions of a reference standard, and the resulting calibration curve is then used to then determine the amount of antigen present in the unknown. Although used as the current gold standard, it is well-known that the SRID assay for influenza potency determination is fraught with uncertainty [Minor, P. D. "Vaccines against seasonal and pandemic influenza and the implications of changes in substrates for virus production", Clinical Infectious Diseases, 2010, 50, 560-565. and references therein].

While the reference standards are provided at no cost by the Center for Biologics Evaluation and Research (CBER), additional materials must be purchased and prepared by the entity performing the testing. Based on a conservative operating cost of $100 per hour for a small protein manufacturer, the minimal cost per SRID assay is $600. At the research phase, a small-scale influenza vaccine producer typically conducts 20-25 SRID assays per week during the development and testing phase. Thus, the cost of SRID even for small scale R&D can be on the order of $60,000 per month. Perhaps even more important is the development and production delays imposed by the slow turn-around time for the method. Often vaccine producers must wait days for results prior to moving forward in the process, decreasing throughput and efficiency.

In their Fiscal Year 2010 CBER Annual Report, CBER summarized a 3-day workshop held to evaluate lessons learned from potency testing of the pandemic 2009 H1N1 vaccines. The suitability of current methods (SRID) was questioned, and a recommendation was made for improvements to the SRID assay. In addition, a recommendation was made to continue to explore alternative methods and technologies for potential future application. Also, in a talk presented at the USP $2^{nd}$ Bioassay Workshop (Aug. 13, 2009), Dr. Armen Donabedian of Health and Human Services and BARDA called for a wide range of efforts to "improve or replace the SRID assay [to] facilitate seasonal and pandemic influenza preparedness."

US Patent Application Publication No. 2010/0041022, U.S. patent application Ser. No. 12/587,136, filed Oct. 2, 2009, titled Novel Assay for the Separation and Quantification of Hemagglutinin Antigens, which is incorporated herein by reference as if set out in full, describes a high performance liquid chromatography (HPLC) based method for quantification of influenza HA proteins as an alternative to SRID. HPLC methods can work reasonably well but have not been widely adopted, likely, due to the typical drift, instrument maintenance required, poor ease-of-use, and calibration problems associated with HPLC.

US Patent Application Publication Number 2011/0201039 describes a combined liquid chromatography mass spectrometry (LCMS) method for the quantification of viral proteins, targeted towards the quantification of influenza HA protein for use in vaccine production. LCMS in general tends to be too complex for routine use by minimally trained personnel and suffers from many of the same maintenance, ease of use, and calibration issues previously mentioned.

US Patent Application Publication No. 2011/0070574, U.S. patent application Ser. No. 12/994,189, filed Nov. 23, 2010, titled Method for Virus Detection, which is incorporated herein by reference as if set out in full, describes a sensor-based method for determining the concentration of virus or viral antigen based on surface plasmon resonance detection. This method offers improved sensitivity relative to SRID, but is too expensive for routine use by all but the largest vaccine producers and requires large, complex instrumentation.

For steps in the vaccine development process where rapid protein quantification is needed, many vaccine producers rely heavily on enzyme linked immunosorbent assays (ELISA) as an alternative to SRID. In a traditional "sandwich" ELISA assay, an antibody specific to a particular antigen is immobilized on a solid support (such as the bottom of a microtiter plate). An unknown amount of antigen is then added, and binds to the surface-immobilized antibody. After the antigen is immobilized, an enzyme-linked detection antibody is then added and forms a complex with the antigen. Subsequent addition of an appropriate substrate for the enzyme ultimately results in the formation of a detectable signal. In general, ELISA assays are more rapid than SRID (hours versus days).

Although more rapid than SRID, the hands-on time required for sample preparation and analysis for ELISA assays is still costly. A research unit within a large vaccine company may conduct upwards of ~50 ELISA assays per week. Each assay requires 7 serial dilutions per sample and 2 replicates per dilution for both a standard and an unknown sample. Thus, each sample requires 28 preparations. The analysis is typically performed over 2 days; plates are prepared on day one, with 4-6 hours of incubation/analysis on the second day. The estimated costs for materials and labor for each protein sample quantified by ELISA is $300-$400 USD, such that the cost for a lab that conducts 50 ELISAs per week is $70,000 USD per month or $840,000 USD per year. During production at a medium scale facility, the costs associated with materials, labor, and time delays are estimated to exceed several million USD per year.

Other technical disadvantages of ELISA methods include the fact that the signal is generated by an enzymatic reaction as a function of time, requiring critical timing of the reaction and inclusion of a standard with every batch of samples. Also, the enzymatic reaction must be stopped after a specified period time using a "stopping agent", and quantification must be conducted within 2 hours of the addition of the stopping agent.

After a vaccine is developed, its efficacy must be evaluated in clinical trials whereby the immune response is evaluated following vaccination. The current gold standard assay for the evaluation of post-vaccination efficacy of a number of viral vaccines, including vaccines for influenza viruses, is the hemagglutinin inhibition (HI) assay which involves semi-quantification of antibodies within patient serum following vaccination. The HI assay is based on the underlying hemagglutination assay ('HA assay') for semi-quantification of hemaglutinin (HA) protein concentration. The HA surface protein on influenza virus particles are known to bind to red blood cells and hemagglutinate (forming an extended lattice-type structure). To perform the HA assay, a series of dilutions of an influenza-containing sample are prepared, and each dilution is mixed with a known amount of red blood cells, (typically in a microtiter plate). Red blood cells that are not bound in the lattice structure due to the presence of influenza virus precipitate to the bottom of the well, whereas the red blood cells that are bound to influenza particles form a lattice that coats the well. The HI assay used for vaccine efficacy evaluation takes advantage of the fact that antibodies to influenza virus that should be present after vaccination will inhibit hemagglutination due to the binding of the antibodies to the HA surface proteins. Serum obtained from a vaccinated individual is collected, and serial dilutions of the serum are added to wells each containing a known amount of red blood cells and antigen (influenza virus). The HI titer of the serum sample is determined as the highest dilution that prevents hemagglutination. In the absence of appropriate anti-HA antibodies (in an unvaccinated individual, for example), hemagglutination would be observed.

There are several practical limitations to traditional HA and HI assays. The 2002 World Health Organization Manual on Animal Influenza Diagnosis and Surveillance outlines the importance of preparing fresh antigen solutions, standardization of the protocol for red blood cell suspension, strict adherence to proper incubation times, and prompt visual "reading" of the plates after the assay is completed. In addition, non-antibody inhibitors can also exist that inhibit hemagglutination and can cause incorrect interpretation. Moreover, the HA and HI assays is limited by the subjective nature of the visual readout. Because the detection relies on interpretation of the hemagglutination pattern present in the wells, abnormal hemagglutination patterns can complicate the interpretation. In addition, a two-fold difference in HI titer is generally considered within the variability of the test and not considered significant.

In view of the foregoing, there is a clear and considerable need in the art to overcome the time, cost, and complexity limitations associated with existing protein and antibody quantification methods including SRID, ELISA, HI assay methods in the fields of vaccine-related protein quantification, potency determination, and efficacy evaluation. The technology of the present application addresses these and other limitations in the current state of the art.

SUMMARY OF THE INVENTION

The technology of the present application provides improved methods for the quantification of influenza HA proteins and anti-influenza antibodies for the fields of vaccine-related protein quantification, potency determination, and efficacy evaluation which provides improvements over the many drawbacks associated with the current state of the art assays. In some embodiments, quantification according to the present application is achieved by providing a plurality of capture agents attached to an array, said capture agents being affixed to the array at a series of decreasing concentrations. In some embodiments, serial dilutions of a reference material are introduced, each dilution being contacted with a separate identical array. The reference material within each solution then binds to the corresponding capture agents on the array and is subsequently labeled with an appropriate label agent capable of producing a detectable signal. The detectable signals from each array for each concentration of reference material are used to construct a calibration curve. A target material of unknown concentration is introduced to a separate identical array, and the target material binds to the capture agents on the array and is labeled by an appropriate label agent to produce a detectable signal. The calibration curve based on the reference material is then utilized to determine the concentration of target material present without the need to perform replicate experiments on serial dilutions of the target. In some embodiments, the capture agents are strain-specific influenza anti-HA antibodies. In other embodiments, the capture agents are universal anti-influenza antibodies. In other embodiments, the capture agents are sialic acid glycoproteins. In even other embodiments, the capture agents are influenza hemagglutinin proteins.

The foregoing and other features, utilities, and advantages of the technology of the present application will be apparent from the following more particular detailed description of the technology as illustrated in the accompanying drawings.

BRIEF DESCRIPTION OF THE DRAWINGS

A better understanding of the technology of the present application will be had upon reference to the following detailed description read in conjunction with the accompanying drawings. In the accompanying drawings, like reference characters refer to like parts throughout, and wherein:

FIG. 8 illustrates a single capture event on an array involving HA antigen as capture agent, an anti-influenza antibody as target or reference material, and a fluorescently labeled universal antibody or antibody fragment as a label agent

DETAILED DESCRIPTION

Figure 1:
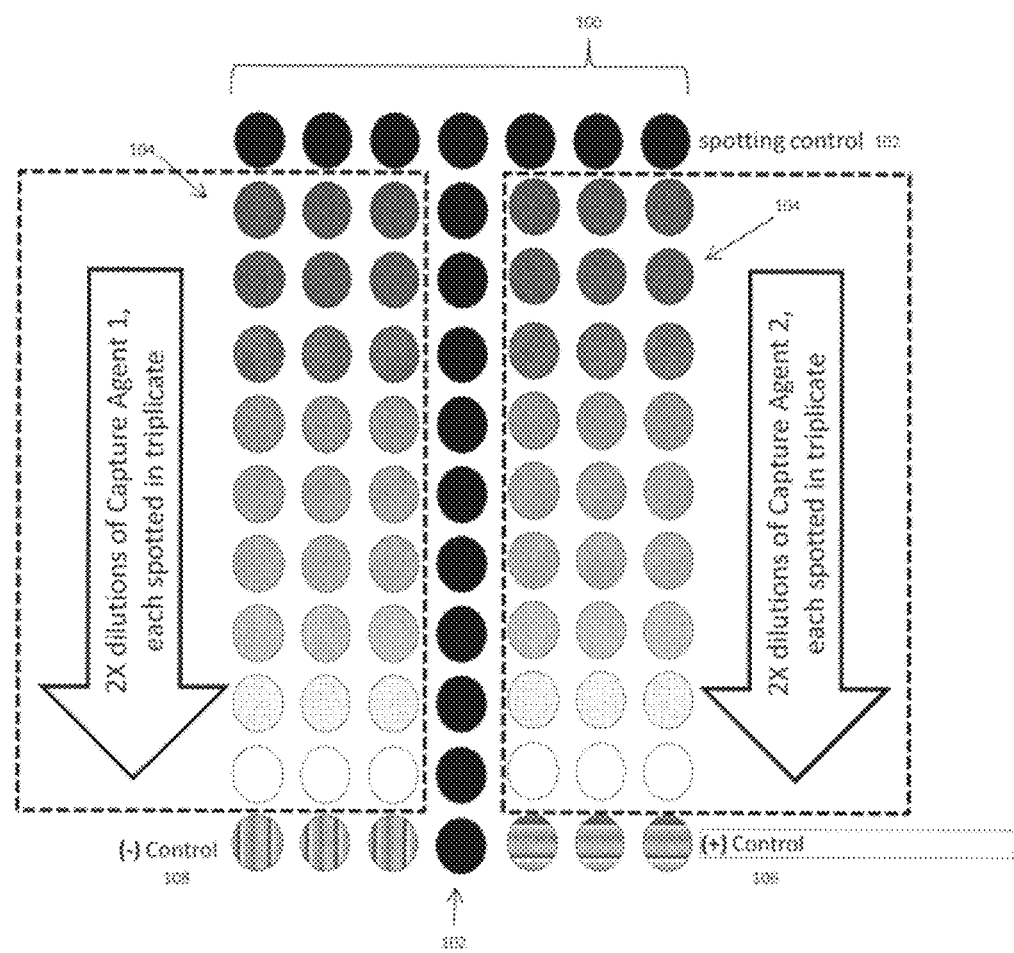
FIG. 1 is a representative array layout of the current invention including serial dilutions of two unique capture sequences, a positive control, a negative control, and a spotting control

As mentioned previously, the technology of the present application relates to methods for improved vaccine-related protein quantification, potency determination, and efficacy evaluation using an array-based format in which serial dilutions of an appropriate capture agent are printed. Detectable signals from replicate arrays contacted with different concentrations of a reference material are analyzed, and the maximum signal achieved for each concentration determined from a non-linear regression to the binding curve data is then used to construct a one-time calibration curve; the calibration curve can then be used to quantify a target material after a single concentration of said target material has been contacted with a replicate array and a detectable signal is produced. The technology of the present application provides significant advantages over the current state of the art methods in that a single concentration of target material(s) can be used to obtain the concentration of said target material(s) due to array encoded serial dilution of the capture agent, and that the quantification of multiple targets can be achieved in a single assay due to the multiplexing capability of an array-based approach. Moreover, while the technology of the present application is described in relation to influenza, one of ordinary skill in the art will understand on reading the present application that the technology may be used for many different viral proteins, and other protein biomarkers. Additionally, the below detailed description of the technology of the present application is provided with regard to certain exemplary embodiments. The word "exemplary" is used herein to mean serving as an example, instance, or illustration. Any embodiment described herein is not necessarily to be construed as preferred or advantageous over other embodiments. If a single exemplary embodiment is provided for completeness, it is not to be concluded that no other embodiments are possible. Moreover, all embodiments described herein should be considered exemplary unless otherwise stated.

For the purposes of the present application, an array refers to any solid support onto which a specific arrangement of capture agents can be placed onto one or more of its surfaces. The solid support can be constructed of but is not limited to glass, plastic, silicon-coated substrate, macromolecule-coated substrate, membrane or filter material, metal, particles or microparticles, beads or microbeads, magnetic or paramagnetic beads, or a variety of other materials known to those skilled in the art. In one embodiment of the current invention, the arrangement of capture agents upon said array are in discrete regions or locations, with each region or location containing only one specific capture agent, so as to create a specific pattern or configuration of capture agents. While provided in discrete regions or locations in the exemplary embodiments, in certain embodiments the capture agents may be provided in a contiguous region having delineated concentrations or the like.

In reference to the present application, a capture agent refers to anything that can be immobilized on the surface of said array that will capture or bind to a target material. For the purposes of the current invention, capture agents include any number of biological molecules including proteins, monoclonal and polyclonal antibodies, antisera, antigens, polypeptides, viral epitopes, cell membrane receptors, glycoproteins, glycopeptides, sugars, and other similar species known to those skilled in the art. In one embodiment of the technology, capture agents are designed to bind appropriate reference and target materials from a solution applied to the array for the purposes of detecting the presence and quantity of said reference and target materials.

For the purposes of the present application, reference material refers to any material of known concentration that can be used to construct a calibration curve based on the magnitude of detectable signals created by the binding event between capture agent(s) and reference material(s). As a non-limiting example, in the present application, reference material may refer to a standard influenza antigen from which a calibration curve of influenza hemagglutinin (HA) concentration can be created. As another non-limiting example, reference material may refer to standard anti-influenza antibody/antibodies from which a calibration curve of antibody concentration can be created.

A target material, for the purposes of the present application, is a material from the same family as the reference material (e.g. as a non-limiting example, both the reference and target materials are influenza HA antigens or are both anti-influenza antibodies) that is present at an unknown concentration and whose concentration can be quantified by utilizing a calibration curve constructed from a reference material.

For the purposes of the present application, a label agent is any species that can be utilized to detect the presence of target material on an array by exhibiting a detectable signal. For the purpose of the present application, a label agent could be an antibody capable of binding to the target agent that is either directly conjugated to a fluorescent molecule or entity, or conjugated to another moiety capable of subsequently binding to a fluorescent molecule or entity. In addition, a label agent could be a fluorescent molecule designed to be incorporated directly into the target agent by means known to those of ordinary skill in the art. In other embodiments of the technology, the detectable signal is based on a property other than fluorescence, including absorbance, chemiluminescence, electrical signal, or other signal types known to those skilled in the art.

The illustrative example shown in FIG. 1 details a typical layout of an array 100 of the present application. In one embodiment of the technology, a spotting control 102 is utilized to provide spatial orientation. Advantageously, the spotting control can also be utilized to normalize the detectable signals from the reference and target materials. In FIG. 1, with exception of the spotting control, all other capture agents 104 spotted on the array are spotted in triplicate (3 contiguous spots in a row). In another embodiment as shown in FIG. 1, the array 100 layout also contains a positive control 106 designed to validate the assay is functioning properly. In yet another embodiment as shown in FIG. 1, a negative control capture agent 108 (designed not to bind to the reference or target agents) is also included to determine if non-specific binding is occurring. In other words, if the negative control provides a detectable signal, the results of the array 100 are suspect. Advantageously, each dilution within a dilution series of a particular capture agent is spotted in triplicate in a defined configuration. FIG. 1 shows a non-limiting example in which two unique capture agents are spotted on the array. Each dilution within the series is spotted in triplicate. Advantageously, the dilution series of the capture agent(s) covers a broad concentration range that encompasses all key regions of a binding curve. In another embodiment of the technology, the array can be spotted within a flat-bottomed 96 well plate or other methods conventionally known to those of ordinary skill in the art for easy integration into existing laboratory systems. Regardless of the particular nature of the capture agent, reference, and target agents, a similar array layout can be used.

In current state of the art immunoassays, such as SRID or ELISA, the unknown target antigen concentration is determined from the linear portion of the calibration curve constructed from a serial dilution of a known, or standard, antigen concentration. The key mathematical relationships are described in Equations 1 and 2 below:

$$S_{kn} = m_{kn} C_{kn} + S_o \quad \text{(Equation 1)}$$

$$C_{unk} \cong S_{unk}/m_{kn} \quad \text{(Equation 2)}$$

where in Equation 1, $S_{km}$ is the detectable signal from a standard as a function of known concentration ($C_{kn}$), $m_{kn}$ is the slope of the linear portion of the calibration curve, and $S_o$ is the background signal. Once the calibration curve is constructed, a serial dilution of the unknown is also analyzed to ensure that the signal is within the linear portion of the calibration curve. For those dilutions in the linear range, the unknown concentration can be obtained from the relationship shown in Equation 2, where $C_{unk}$ is the unknown antigen concentration, $S_{unk}$ is the signal for the unknown antigen concentration, and $m_{kn}$ is the slope of the linear portion of the calibration curve.

Figure 2:
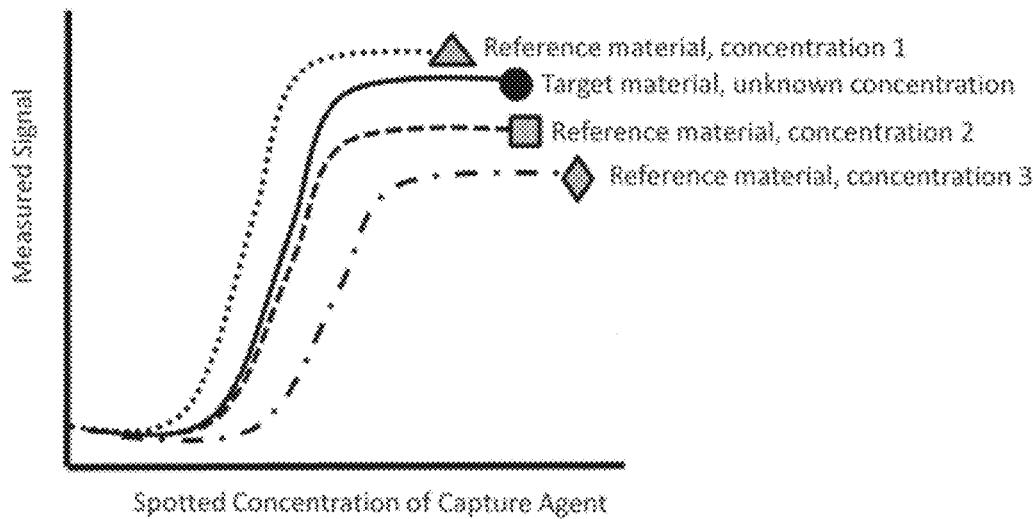
FIG. 2 is a schematic representation of the binding curves generated from reference material(s) and target used to construct a calibration curve and subsequently determine the unknown concentration of target
Figure 2:
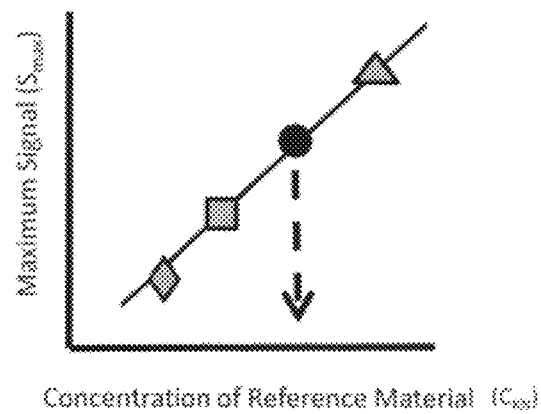

In contrast to the above mentioned SRID and ELISA methods, the technology of the present application provides a method for which the analysis of a single concentration of unknown target material results in a complete binding curve. Consider the binding curve obtained for a single concentration of target or reference material shown pictorially in FIG. 2A and described by Equation 3 below:

$$S = S_o + \frac{S_{max}}{1 + (C_{im})^A} \quad \text{(Equation 3)}$$

where S is the signal from the single concentration of target or reference material as a function of immobilized capture agent concentration ($C_{in}$), $S_o$ is the background signal, $S_{max}$ is the maximum value of the signal obtained, and A is related to the slope of the binding curve. The maximum signal ($S_{max}$) extracted from a non-linear regression to the data is directly proportional to the target or reference concentration and is used for quantification, rather than relying on the slope. Several dilutions of a reference material of known concentrations are prepared and applied to replicate arrays, and the binding curves for the reference material (dotted, dashed, and dash-dotted Reference material binding curves shown in FIG. 2A) are then used to construct a calibration curve by subsequently plotting $S_{max}$ versus $C_{kn}$, as graphically illustrated in FIG. 2B. A single concentration of target material is then applied to a replicate array, a non-linear regression to the data is applied, and the maximum value ($S_{max}$) obtained (solid black Target material binding curve in FIG. 2A). The equation of the calibration curve can then be used to solve for the unknown concentration of target material.

The technology of the present application is advantageous over the state of the art methods for a number of reasons. One reason is that all signals can be normalized to an internal reference ($S_{iref}$) that is encoded on the array. As a non-limiting example, the spotting control shown in FIG. 1 can be used as $S_{iref}$. Specifically, the $S_{max}$ value is divided by $S_{iref}$ (i.e., $S_{max-norm} = S_{max}/S_{iref}$) to yield a signal normalized for random experimental variables (e.g., chip to chip variations). The ramification of this advantage is that the current method does not require a complete serial dilution of the standard for each batch of samples analyzed. In principle, for a given set of experimental conditions (e.g., influenza HA from recombinant baculovirus expression), a single serial dilution of the standard could be used to determine the concentration of large number of sample batches using $S_{max-norm}$ in a calibration curve (see FIG. 2B).

In another embodiment, numerous capture agents could be immobilized on the array to take advantage of multiplexing, allowing multiple target antigens (for example, HA antigens from influenza A H1N1, influenza A H3N2, and influenza B) could be quantified simultaneously in a multiplex analysis, thereby dramatically reducing the total number of assays required to quantify the targets of interest. This specific example could be utilized in potency determination in yearly trivalent influenza vaccines to speed the development time.

Several non-limiting examples follow to further explain and illustrate the advantages of the technology over the state of the art.

Figure 3:
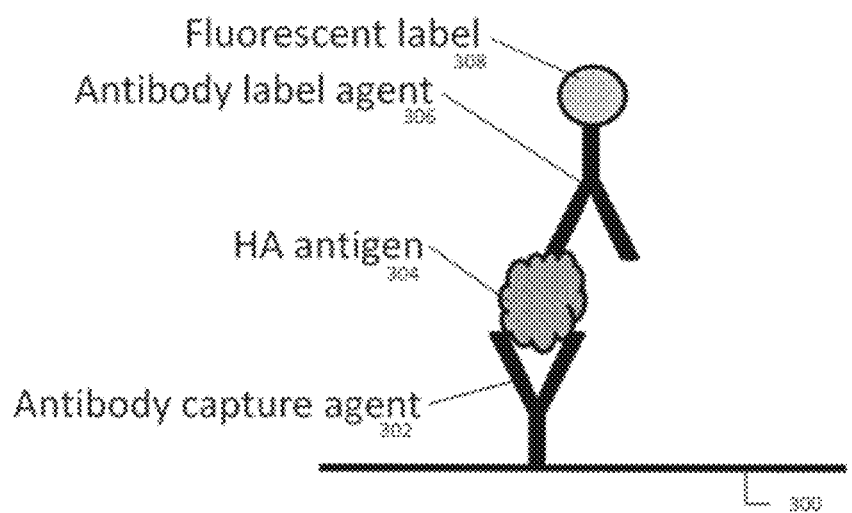
FIG. 3 illustrates a single capture event on an array involving an antibody as capture agent, antigen as target or reference material, and a fluorescently labeled antibody as a label agent
Figure 4:
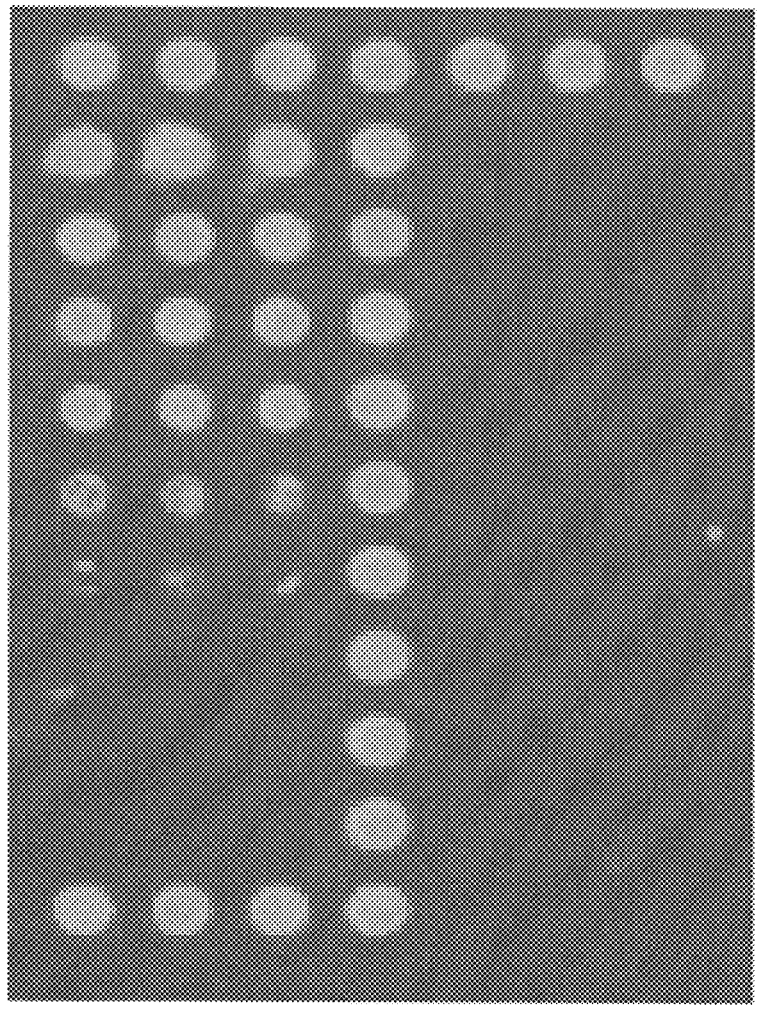
FIG. 4 is a fluorescence image of an array containing serial dilutions of an anti-human influenza A H3 antibody as capture agent, purified influenza HA H3 antigen as reference material, and a fluorescently labeled universal antibody as label agent
Figure 5:
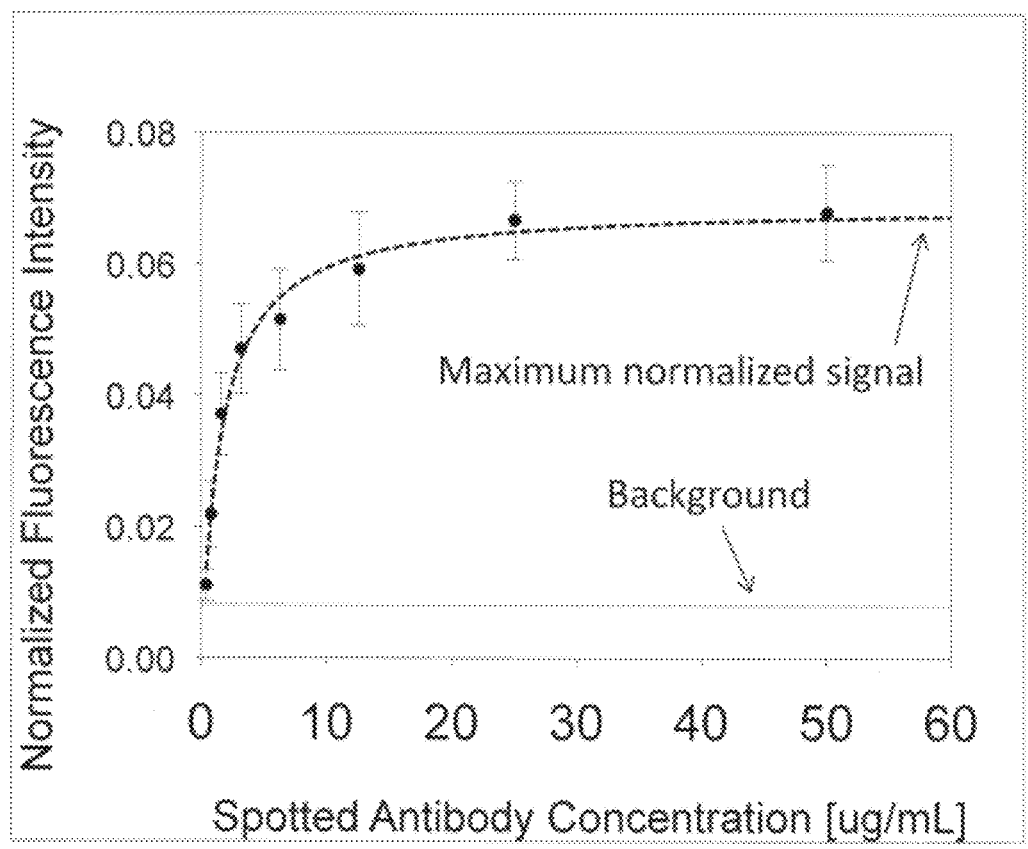
FIG. 5 is a binding curve obtained from the analysis of the detectable fluorescence signals obtained after exposing the array represented in FIG. 4 to 0.5 µg/mL of H3 HA reference material.
Figure 6:
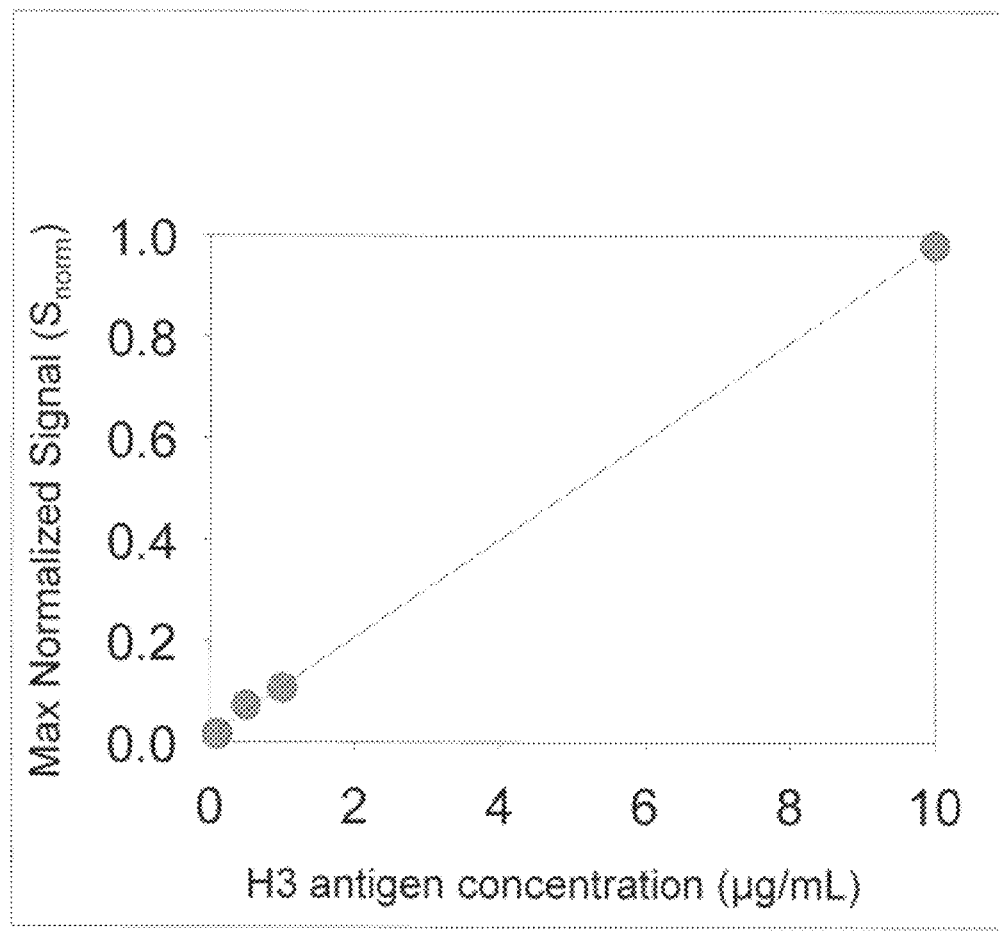
FIG. 6 is a linear regression obtained by plotting the normalized maximum signal obtained for serial dilutions of HA reference material added to identical replicate arrays
Figure 7:
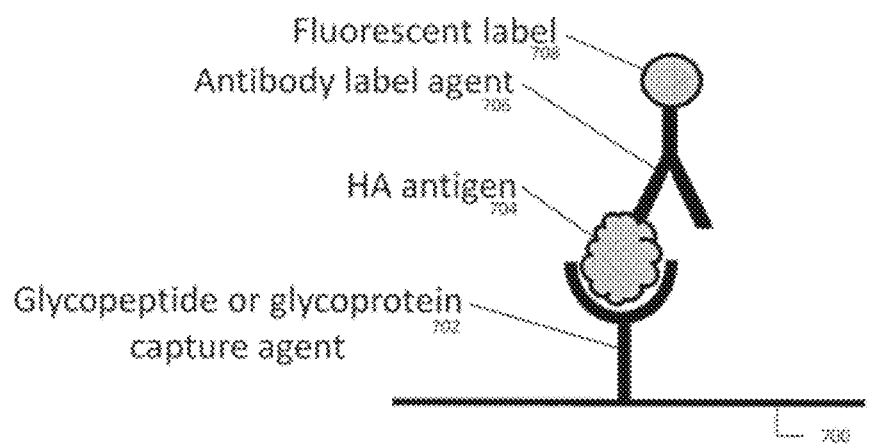
FIG. 7 illustrates a single capture event on an array involving a glycopeptide or glycoprotein as capture agent, influenza HA from a vaccine as target or reference material, and a fluorescently labeled universal antibody or antibody fragment as a label agent

Quantification of Influenza HA Using Strain-Specific Capture Antibodies for Influenza Vaccine Potency Determination In an illustrative example of the technology of the present application, subtype-specific monoclonal antibodies against influenza A H3 HA and influenza A H1 HA (Meridian, catalog #C01318M and #C86304M) were printed onto aldehyde-functionalized glass slides in the layout illustrated in FIG. 1, with the anti-H3 antibody represented by Capture Agent 1 (104, left-hand side of array layout) and the anti-H1 antibody represented by Capture Agent 2 (104, right-hand side or array layout). The general detection scheme for this example is schematically shown for a single binding event is shown in FIG. 3. For reference, FIG. 3 provides an exemplary array 300 consistent with the technology of the present application. Array 300 having a discretely located capture agent 302. The capture agent 302 binds in this exemplary embodiment to the HA antigen 304. An antibody label agent 306 binds the HA antigen 304 to a fluorescent label 308, which is capable of detection as is generally known in the art.

Serial dilutions of H3 hemagglutinin (HA) antigen from the influenza A H3N2 strain A/Wy/3/2003 (Protein Sciences Corporation, Meriden, Conn.) in phosphate buffer were each incubated on separate replicate microarrays at room temperature for 1 hr. After subsequent washing, the captured HA antigen was labeled with a universal biotinylated anti-HA antibody fragment (Sigma Aldrich, catalog #B9183) followed by a Cy3-labeled streptavidin at 1.2 μg/mL. The universal antibody label utilized was raised against a universal HA peptide often used as a tag in recombinant proteins, and has demonstrated response to a conserved region of both native and denatured HA.

A representative fluorescence image for a single H3 HA concentration applied to the array (0.5 μg/mL) is shown in FIG. 4. The normalized signal intensity from the fluorescence image as a function of the spotted anti-H3 antibody concentration was fit to Equation 3 using non-linear regression and the maximum signal achieved determined, as shown in FIG. 5. Only a limited range of HA concentrations were examined for this example, and the maximum signals determined for these different concentrations are plotted in FIG. 6. As expected, the extracted $S_{norm}$ value (plotted on the y-axis of FIG. 6) for this limited range of H3 HA concentrations is linear as determined by regression. It is anticipated from extrapolation that the quantification of the technology of the present application should be below 0.1 μg/mL. Considering that the currently used SRID assay has a quantification limit of ~2-5 μg/mL, the technology of the present application would have an improved limit of detection over current state of the art methods and therefore provide benefits over the current state of the art to vaccine manufacturers.

Quantification of Influenza HA Using Universal Capture Agent(s) for Influenza Vaccine Potency Determination As previously mentioned, the traditional SRID assay requires the development and use of well characterized standard reference antibodies and antigens for each new strain of influenza produced. Since influenza viruses continually evolve, new standards must be produced in response to the emergence of each seasonal virus. Thus, the generation of these standard materials (e.g., antibodies and antigens) often represent a bottleneck in influenza vaccine development. Vaccine manufacturers must often wait to obtain reference materials from the Center for Biologics Evaluation and Research (CBER).

In one embodiment of the technology described herein, stable and universal standards used as capture agent(s) on an array for determination of influenza vaccine potency would streamline vaccine production by reduction of "wait time" for new reference antibodies and antigens and allow for improved quality control and assurance through historical trends with respect to a single reference standard (rather than relying on new unique standards each year for each strain of virus).

In another embodiment of the technology described herein, α2,6 and α2,3 sialic acid glyopeptides or proteins are used as capture agents to determine influenza vaccine potency. In the influenza viral infection process, influenza HA on the surface of the virus particle binds to sialic acid receptors on the host cell surface. It is well-known that influenza viruses from different host species vary in their affinity for sialic acid receptors with different linkages. Specifically, influenza viruses that replicate in humans selectively bind to the α2,6 sialic acid found on the surface of human respiratory epithelial cells, whereas influenza viruses that replicate in birds selectively bind to the α2,3 sialic acid found on the surface of epithelial cells found in the waterfowl gut.

Typical gold standard potency assays are based on the two irresolvable experimental parameters of concentration and binding constant. By utilizing the ratio of detectable signals produced on an array for the two types of receptors, the concentration and binding constant can be separated. As a non-limiting example, with α2,6 and α2,3 sialic acid glyopeptides or proteins, the relative binding strength of a target HA to both types of sialic acid glycopeptides or glycoproteins could be measured in a single assay. Mathematically, if we neglect the labeling step, the separation of variables can be shown by:

$$S_{max,\alpha2,6} \propto K_{\alpha2,6}[C_{HA}] \quad \text{(Equation 4)}$$

and $$S_{max,\alpha2,3} \propto K_{\alpha2,3}[C_{HA}] \quad \text{(Equation 5)}$$

where $S_{max}$ is the maximum signal obtained from a binding curve as described in Equation 3, $K_x$ is the binding constant, and $C_{HA}$ is the concentration of HA in solution applied to the microarray. Since the concentration of HA for both is the same, the relationship below follows:

$$\frac{S_{max,\alpha2,6}}{S_{max,\alpha2,3}} \propto \frac{K_{\alpha2,6}}{K_{\alpha2,3}} \quad \text{(Equation 6)}$$

This ratio may be a more direct measurement of vaccine potency, as a theoretical quantitative value can be determined from insight into cell receptor composition for each species (e.g. α-2,6 for human, α-2,3 for avian, and a mixture of receptors, therefore an intermediate ratio, for swine). As a non-limiting example, optimal potency of a human influenza vaccine would produce a high signal ratio in Equation 6 due to the much higher binding constant for HA to the human α-2,6 sialic acid (Kα2,6>>Kα2,3).

To overcome the limitations associated with the current gold standard SRID assay, a sialic acid glycoprotein(s) or glycopeptide(s), in combination with a strain-independent label, can be developed, fully characterized, and used as a universal reference for determining influenza vaccine potency. The detection scheme for this non-limiting example is schematically illustrated in FIG. 7, where an immobilized glycopeptide or glycoprotein acts as capture agent. Serial dilutions of α-2,6 and α-2,3 sialic acid glyopeptide(s) or protein(s) are configured in an array. Influenza HA antigen is allowed to bind to the array and is subsequently labeled with a label agent. In one embodiment of the current invention, the label agent is a fluorescently tagged, strain-independent anti-HA antibody fragment (such as monoclonal anti-HA #H9037 from Sigma Aldrich). For reference, FIG. 7 provides an array 700 consistent with the technology of the present application. Discretely located on array 700 are a series of glycopeptides or glycoprotein capture agents 702 that capture or bind an associated HA antigen 704. An antibody label agent 706 binds the HA antigen 704 to a fluorescent label 708, which is capable of detection as is generally known in the art.

Hemagglutinin Inhibition Assay on an Array for Influenza Vaccine Efficacy Determination As previously mentioned, the principle of the hemagglutinin inhibition (HI) assay is that antibodies will prevent the agglutination of red blood cells by influenza viruses. For influenza viruses, agglutination refers to the process whereby the virus binds to sialic acid receptors on cell surfaces and can cause the cells to aggregate around the virus. Aggregation leads to cell complexes that prevent red blood cells from settling to the bottom of a well. The assay is conducted by serial dilution of patient serum mixed with a specific concentration of virus and red blood cells whereby the highest dilution of the patient serum that prevents hemagglutination is the HI titer value.

To overcome the aforementioned limitations associated with the current gold standard HI assay for influenza vaccine efficacy, a reference standard of influenza hemagglutinin (HA) is used as a capture agent where serial dilutions of the HA standard(s) is/are configured onto an array under carefully controlled and reproducible conditions. The array of HA antigen(s) is then used to quantify antibodies in serum obtained from a patient that are developed in response to an influenza vaccination. The detection scheme for this non-limiting example of the current invention is illustrated in FIG. 8, where standard HA antigen is used as a capture agent. HA antigen is configured onto an array, antibodies produced in response to the vaccination from patient serum are captured on the array, and the captured antibodies are subsequently labeled with a label agent to produce a detectable signal. In the current non-limiting example, the label agent is a fluorescently tagged anti-human antibody. The patient produced antibodies are quantified by the value of $S_{max-norm}$ mapped to a calibration curve generated by serial dilutions of a reference antibody, similar to the process described previously and schematically represented in FIG. 2. Advantages of this example of the current invention are the quantitative nature of the assay where if the binding constant is known, the concentration determined can be expressed in absolute terms and compared to results from other common measurements of protein quantification (e.g. pg/mL or moles/mL). In addition, this example produces a rapid time to result, is automatable, and eliminates the use of red blood cells the assay. For reference, FIG. 8 provides an array 800 consistent with the technology of the present application. Discretely located on array 800 are a series of HA antigen capture agents 802 that capture or bind an associated target material 804, which is an antibody in this exemplary embodiment. An antibody label agent 806 binds the target material 804 to a fluorescent label 808, which is capable of detection as is generally known in the art. Unless otherwise indicated, all numbers or expressions, such as those expressing dimensions, physical characteristics, etc. used in the specification are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

I claim:

1. A method for the quantification of an amount of influenza hemaglutinin HA present in a sample comprising the steps of:
   (a) immobilizing a plurality of capture agents onto a provided array, said provided array comprising a solid support onto which said plurality of capture agents affixed to the solid support in a plurality of discrete areas, said plurality of discrete areas only containing a single unique capture agent and arranged in a configuration of decreasing concentration of said single unique capture agent;
   (b) contacting (i) at least three replicates of said array with a reference material so as to allow binding between said reference material and said plurality of capture agents, each replicate of said array being contacted with a different concentration of said reference material and (ii) a replicate of said array with at least one target material so as to allow binding between said at least one target material and said plurality of capture agents;
   (c) contacting said replicates of said array with at least one antibody label agent to produce a detectable signal indicative of said binding between reference or target material(s) and capture agent(s);
   (d) processing said detectable signals of said replicates of said array using a ratio of said detectable signals to detectable signals from an internal reference encoded on said array to yield a normalized signal;
   (e) constructing a concentration calibration curve comprising the normalized signals of said replicates of said array as a function of the concentration of reference material applied to said replicates of said array, wherein said constructing step uses a maximum signal response achieved on each array for each concentration of said reference and said target material;
   (f) analyzing the concentration calibration curve using linear regression to provide linear regression parameters; and
   (g) quantifying the amount of said target material(s) using said linear regression parameters and the detectable signal indicative of binding between the target materials(s) and the capture agent(s);
   wherein the plurality of capture agents comprise a first anti-influenza A H1 antibody capture agent, a second anti-influenza A H3 antibody capture agent and a third anti-influenza B antibody capture agent, and
   wherein the reference and target materials are influenza hemagglutinin.

2. The method of claim 1, wherein contacting multiple replicates of said array with a reference material precedes contacting a replicate of said array with at least one target material.

3. The method of claim 1, wherein contacting multiple replicates of said array with a reference material is subsequent to contacting a replicate of said array with at least one target material.

4. The method of claim 1, wherein the minimum number of dilutions of the plurality of capture agents on the array required to generate a binding curve is 3.

5. The method of claim 1, wherein the detectable signals are fluorescence signals.

6. The method of claim 1, wherein the detectable signals are optical, colorimetric, electrical, or magnetic.

7. The method of claim 1, wherein the anti-influenza A H1 antibody is a monoclonal antibody specific to influenza A H1.

8. The method of claim 7, wherein the influenza A H1 is influenza A H1N1.

9. The method of claim 1, wherein the anti-influenza A H3 antibody is a monoclonal antibody specific to influenza A H3.

10. The method of claim 1, wherein the sample is comprised of material from an influenza vaccine production process.

11. The method of claim 9, wherein the influenza A H3 is influenza A H3N2.

12. The method of claim 1, wherein the multiple replicates of the array in step (b) are provided on a single solid support.

13. The method of claim 1, wherein the detectable signals are detected by exposing the array to an optical imager.

14. The method of claim 13, wherein the optical imager is a fluorescence imager.

15. The method of claim 1, wherein the array further comprises a spotting control affixed to the solid support.

16. The method of claim 15, wherein the spotting control is used to normalize detectable signals from the reference and target materials.

17. The method of claim 15, wherein the array comprises a plurality of discrete spotting control areas.

18. The method of claim 1, wherein the array further comprises at least one positive control affixed to the solid support.

19. The method of claim 1, wherein the array further comprises at least one negative control capture agent affixed to the solid support.

20. The method of claim 1, wherein the array further comprises:
a spotting control affixed to the solid support;
at least one positive control affixed to the solid support; and
at least one negative control capture agent affixed to the solid support.

21. The method of claim 20, wherein the spotting control is used to normalize detectable signals from the target materials.

22. The method of claim 20, wherein the array comprises a plurality of discrete spotting control areas.

23. A method of determining the quantity of an unknown amount of influenza hemagglutinin in a sample, the method comprising:
(a) immobilizing a plurality of capture agents onto a provided array, said provided array comprising a solid support onto which said plurality of capture agents are affixed in a plurality of discrete areas, wherein the plurality of capture agents comprises (i) monoclonal anti-influenza A H1 antibody, (ii) monoclonal anti-influenza A H3 antibody and (iii) monoclonal anti-influenza B antibody, wherein each of said plurality of discrete areas contains only one of said plurality of capture agents, and wherein the plurality of discrete areas are arranged in a configuration of decreasing concentration of said capture agent;
(b) contacting at least three replicates of said array with a reference influenza hemagglutinin to allow binding between said reference influenza hemagglutinin and said plurality of capture agents, each replicate of said array being contacted with a different concentration of said reference influenza hemagglutinin;
(c) contacting said replicates of said array with the sample to allow binding between the unknown amount of influenza hemagglutinin in the sample and said plurality of capture agents;
(d) contacting said replicates of said array with at least one label agent to produce a detectable signal indicative of said binding between reference or target influenza hemagglutinin and capture agents;
(e) processing said detectable signals of said replicates of said array using a ratio of said detectable signals to detectable signals from an internal reference encoded on said array to yield a normalized signal;
(f) constructing a concentration calibration curve comprising the normalized signals of said replicates of said array as a function of the concentration of reference material applied to said replicates of said array, wherein said constructing step uses a maximum signal response achieved on each array for each concentration of said reference and said target material;
(g) analyzing the concentration calibration curve using non-linear regression to provide non-linear regression parameters;
(h) quantifying the amount of said influenza hemagglutinin in the sample using said non-linear regression parameters and the detectable signal indicative of binding between the target influenza hemagglutinin and the capture agents; and
(i) determining:
(i) the presence of influenza A H1 hemagglutinin in the sample by observing a detectable signal in at least one of said plurality of discrete areas containing the monoclonal anti-influenza A H1 antibody,
(ii) the presence of influenza A H3 hemagglutinin in the sample by observing a detectable signal in at least one of said plurality of discrete areas containing the monoclonal anti-influenza A H3 antibody, and/or
(iii) the presence of influenza B hemagglutinin in the sample by observing a detectable signal in at least one of said plurality of discrete areas containing the monoclonal anti-influenza B antibody.

24. The method of claim 23, wherein the monoclonal anti-influenza A H1 antibody is a monoclonal antibody specific to influenza A H1.

25. The method of claim 24, wherein the influenza A H1 is influenza A H1N1.

26. The method of claim 23, wherein the monoclonal anti-influenza A H3 antibody is a monoclonal antibody specific to influenza A H3.

27. The method of claim 26, wherein the influenza A H3 is influenza A H3N2.

28. The method of claim 1, wherein the antibody label agent comprises a universal HA antibody label agent against influenza A hemagglutinin.

29. The method of claim 1, wherein antibody label agent comprises a labeled antibody specific for an HA antigen selected from the group consisting of influenza A H1, influenza A H3, influenza B and any combination thereof.

30. The method of claim 1, wherein the anti-influenza B antibody is a monoclonal antibody specific to influenza B.

31. The method of claim 1, wherein the label agent is a fluorescently-labeled antibody.

* * * * *